(12) United States Patent
Amon

(10) Patent No.: US 10,945,760 B2
(45) Date of Patent: Mar. 16, 2021

(54) CANNULATION DEVICE

(71) Applicant: Fresenius Kabi Deutschland GmbH, Bad Homburg (DE)

(72) Inventor: Barbara Amon, Idstein (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 0 days.

(21) Appl. No.: 16/301,123

(22) PCT Filed: Apr. 21, 2017

(86) PCT No.: PCT/EP2017/059503
§ 371 (c)(1),
(2) Date: Nov. 13, 2018

(87) PCT Pub. No.: WO2017/211493
PCT Pub. Date: Dec. 14, 2017

(65) Prior Publication Data
US 2019/0223903 A1    Jul. 25, 2019

(30) Foreign Application Priority Data

Jun. 10, 2016   (EP) .................................... 16173989

(51) Int. Cl.
*A61B 17/34* (2006.01)
*A61M 25/06* (2006.01)
(Continued)

(52) U.S. Cl.
CPC ...... *A61B 17/3421* (2013.01); *A61B 17/3415* (2013.01); *A61B 17/3496* (2013.01);
(Continued)

(58) Field of Classification Search
CPC . A61B 17/34; A61B 17/3401; A61B 17/3415; A61B 17/3494–3498
See application file for complete search history.

(56) References Cited

U.S. PATENT DOCUMENTS 5,066,288 A * 11/1991 Deniega ............. A61B 17/3496
604/117
5,129,884 A    7/1992 Dysarz
(Continued)

FOREIGN PATENT DOCUMENTS

CN    1756572 A    4/2006
CN    201930043 U    8/2011
(Continued)

OTHER PUBLICATIONS

International Search Report and Written Opinion, counterpart International Appl. No. PCT/EP2017/059503 dated Aug. 28, 2017 (9 pages).

(Continued)

*Primary Examiner* — Eduardo C Robert
*Assistant Examiner* — Michelle C Eckman
(74) *Attorney, Agent, or Firm* — Cook Alex Ltd.

(57) ABSTRACT

The invention relates to a cannulation device (1) for providing an access to a patient through a skin of the patient, comprising a puncture needle (11) with a needle tip (113) for puncturing the skin of the patient and a cannula (12). The cannulation device (1) is characterized in that the puncture needle (11) is movably connected to the cannula (12).

12 Claims, 2 Drawing Sheets

Figure 1:
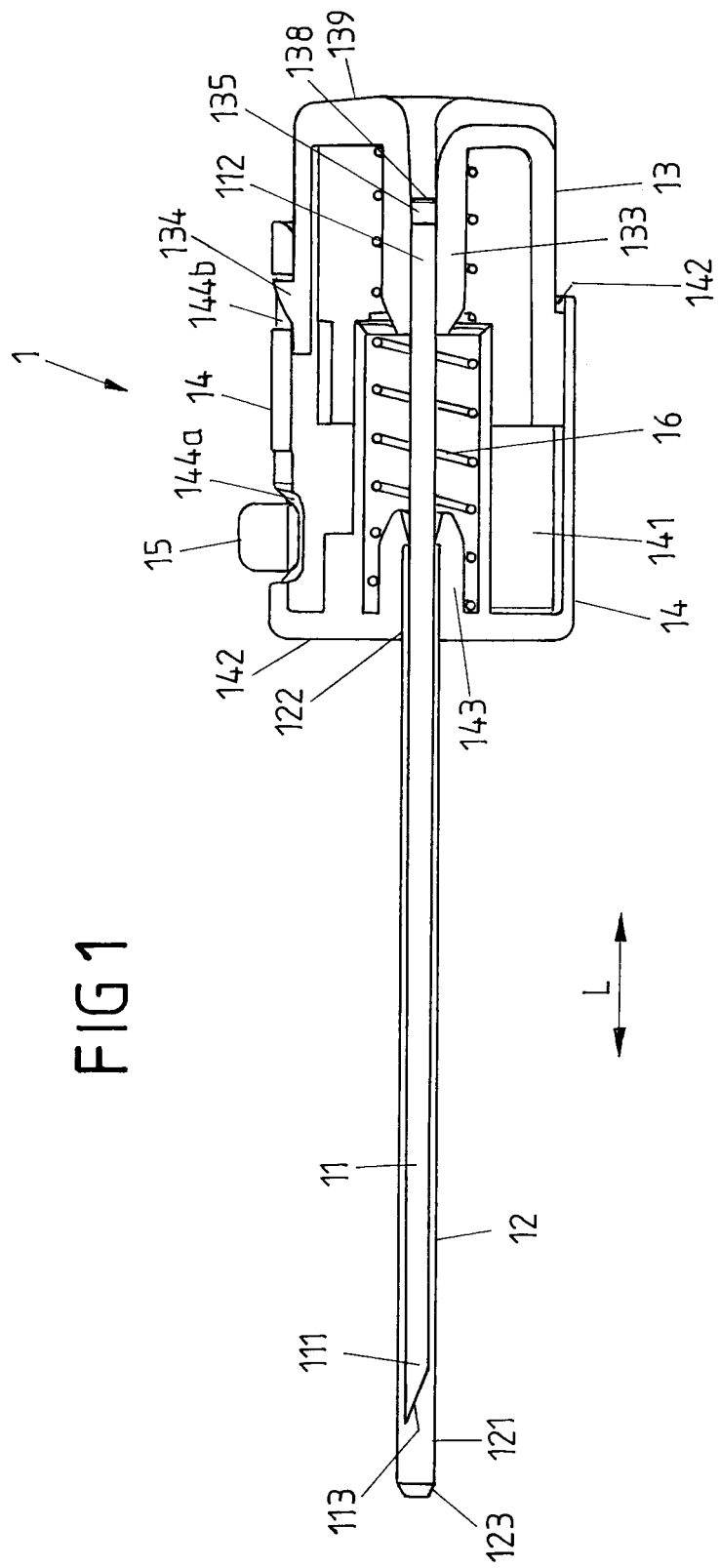

(51) Int. Cl.
*A61M 39/10* (2006.01)
*A61M 5/32* (2006.01)

(52) U.S. Cl.
CPC .... *A61M 25/0606* (2013.01); *A61M 25/0631* (2013.01); *A61M 5/3243* (2013.01); *A61M 39/1011* (2013.01)

(56) References Cited

U.S. PATENT DOCUMENTS

| | | | | |
|---|---|---|---|---|
| 5,318,580 | A * | 6/1994 | Gresl, Jr. | A61B 17/3496 604/164.12 |
| 6,319,266 | B1 * | 11/2001 | Stellon | A61B 17/3496 604/164.01 |
| 2001/0029387 | A1 * | 10/2001 | Wolf | A61B 17/3496 606/184 |
| 2003/0032924 | A1 * | 2/2003 | Scarfone | A61B 17/34 604/117 |
| 2003/0045834 | A1 * | 3/2003 | Wing | A61B 17/34 604/161 |
| 2003/0130621 | A1 * | 7/2003 | Bryan | A61B 17/3401 604/164.01 |
| 2003/0191414 | A1 * | 10/2003 | Reiley | A61B 17/34 600/567 |
| 2004/0059293 | A1 * | 3/2004 | Chu | A61J 15/0015 604/107 |
| 2004/0087914 | A1 * | 5/2004 | Bryan | A61B 17/3401 604/264 |
| 2004/0092879 | A1 * | 5/2004 | Kraus | A61B 17/3415 604/158 |
| 2004/0116856 | A1 * | 6/2004 | Woehr | A61M 5/3273 604/110 |
| 2004/0230160 | A1 * | 11/2004 | Blanco | A61B 17/3421 604/167.06 |
| 2006/0015075 | A1 * | 1/2006 | Blanco | A61B 17/3474 604/264 |
| 2006/0030870 | A1 * | 2/2006 | Staudner | A61B 17/3496 606/167 |
| 2006/0052811 | A1 * | 3/2006 | Blanco | A61B 17/34 606/185 |
| 2006/0155245 | A1 * | 7/2006 | Woehr | A61M 25/0618 604/164.08 |
| 2006/0229528 | A1 * | 10/2006 | Heske | A61B 10/0275 600/567 |
| 2007/0191772 | A1 | 8/2007 | Johnson et al. | |
| 2007/0299459 | A1 * | 12/2007 | Way | A61B 17/34 606/185 |
| 2008/0188812 | A1 * | 8/2008 | Valaie | A61B 17/3415 604/164.01 |
| 2008/0215033 | A1 * | 9/2008 | Miller | A61B 17/3478 604/509 |
| 2008/0228214 | A1 * | 9/2008 | Hoan | A61B 17/34 606/185 |
| 2008/0262431 | A1 * | 10/2008 | Anderson | A61B 17/3415 604/164.1 |
| 2008/0281344 | A1 * | 11/2008 | Morisseau | A61B 17/3496 606/185 |
| 2008/0294111 | A1 * | 11/2008 | Tal | A61M 25/0097 604/165.01 |
| 2009/0069712 | A1 * | 3/2009 | Mulvihill | A61B 10/025 600/564 |
| 2009/0093833 | A1 * | 4/2009 | Smith | A61B 17/3417 606/185 |
| 2009/0131872 | A1 * | 5/2009 | Popov | A61B 17/3415 604/164.08 |
| 2009/0163942 | A1 * | 6/2009 | Cuevas | A61M 16/0472 606/167 |
| 2009/0306697 | A1 * | 12/2009 | Fischvogt | A61B 17/3421 606/185 |
| 2010/0016878 | A1 * | 1/2010 | Smith | A61B 17/3417 606/185 |
| 2010/0063450 | A1 * | 3/2010 | Smith | A61B 17/3417 604/164.01 |
| 2010/0094228 | A1 * | 4/2010 | Bettuchi | A61B 17/3421 604/167.03 |
| 2010/0114110 | A1 * | 5/2010 | Taft | A61B 17/025 606/108 |
| 2010/0268164 | A1 * | 10/2010 | Chung | A61B 17/3421 604/167.03 |
| 2010/0280408 | A1 * | 11/2010 | Rusnak | A61B 10/0233 600/567 |
| 2010/0318033 | A1 * | 12/2010 | Lam | A61B 17/3421 604/164.11 |
| 2011/0087169 | A1 * | 4/2011 | Parihar | A61B 17/34 604/167.03 |
| 2011/0137252 | A1 * | 6/2011 | Oster | A61B 17/3415 604/158 |
| 2011/0276001 | A1 * | 11/2011 | Schultz | A61B 17/3415 604/164.01 |
| 2012/0083661 | A1 * | 4/2012 | Rockrohr | A61B 17/3421 600/208 |
| 2012/0226301 | A1 * | 9/2012 | Geist | A61B 17/3472 606/172 |
| 2013/0102966 | A1 * | 4/2013 | Hanlon | A61B 17/3417 604/164.11 |
| 2013/0237958 | A1 * | 9/2013 | Arrigo | A61M 25/0102 604/506 |
| 2013/0338577 | A1 * | 12/2013 | Al-Habaibeh | A61M 25/0612 604/67 |
| 2014/0025009 | A1 * | 1/2014 | Erskine | A61M 25/0618 604/164.08 |
| 2014/0025036 | A1 * | 1/2014 | Bierman | A61M 25/0097 604/506 |
| 2014/0039534 | A1 * | 2/2014 | Geist | A61B 17/3472 606/172 |
| 2014/0046303 | A1 * | 2/2014 | Donaldson | A61B 17/34 604/540 |
| 2014/0046327 | A1 * | 2/2014 | Tzachar | A61B 17/3472 606/79 |
| 2014/0142542 | A1 * | 5/2014 | Rosenbaum | A61M 25/065 604/506 |
| 2014/0171946 | A1 * | 6/2014 | Benson | A61B 17/1655 606/79 |
| 2014/0276432 | A1 * | 9/2014 | Bierman | A61B 17/3498 604/164.1 |
| 2015/0087914 | A1 * | 3/2015 | Navis | A61M 39/02 600/204 |
| 2016/0007984 | A1 * | 1/2016 | Schaeffer | A61B 17/34 600/210 |
| 2016/0128576 | A1 * | 5/2016 | Chiang | A61B 5/0053 600/587 |
| 2016/0199073 | A1 * | 7/2016 | Nino | A61B 17/1604 606/79 |
| 2016/0220270 | A1 * | 8/2016 | Tamura | A61M 25/0631 |
| 2017/0172567 | A1 * | 6/2017 | Chen | A61B 17/0469 |
| 2017/0311933 | A1 * | 11/2017 | Tanghal | A61B 10/0041 |
| 2017/0319232 | A1 * | 11/2017 | Kiev | A61B 17/32093 |
| 2018/0116693 | A1 * | 5/2018 | Blanchard | A61B 17/3415 |
| 2018/0140286 | A1 * | 5/2018 | Householder | A61B 10/0041 |
| 2018/0169388 | A1 * | 6/2018 | Hung | A61B 17/34 |
| 2018/0214178 | A1 * | 8/2018 | Blanc | A61B 17/34 |
| 2018/0236212 | A1 * | 8/2018 | Chida | A61M 5/00 |
| 2018/0325551 | A1 * | 11/2018 | Kang | A61B 17/3415 |
| 2019/0038876 | A1 * | 2/2019 | Isaacson | A61M 25/065 |
| 2019/0038877 | A1 * | 2/2019 | Isaacson | A61M 25/065 |
| 2019/0083128 | A1 * | 3/2019 | Harder | A61B 17/3415 |
| 2019/0223903 | A1 * | 7/2019 | Amon | A61B 17/3415 |
| 2019/0231389 | A1 * | 8/2019 | Primaz | A61B 17/34 |
| 2019/0255228 | A1 * | 8/2019 | Donaldson | A61B 17/34 |
| 2019/0298240 | A1 * | 10/2019 | Lee | A61B 5/150396 |
| 2019/0298409 | A1 * | 10/2019 | Kucklick | A61B 17/3421 |

FOREIGN PATENT DOCUMENTS

| | | |
|---|---|---|
| CN | 203988167 U | 12/2014 |
| CN | 204394640 U | 10/2015 |
| CN | 205286423 U | 6/2016 |
| EP | 0 653 220 A1 | 5/1995 |
| EP | 1 683 542 A1 | 7/2006 |
| GB | 2503329 A | 12/2013 |

(56) References Cited

FOREIGN PATENT DOCUMENTS

| WO | WO 92/13584 A1 | 8/1992 |
| WO | WO 99/44655 A2 | 9/1999 |
| WO | WO 99/44655 A3 | 9/1999 |
| WO | WO 2006/070358 A2 | 7/2006 |
| WO | WO 2006/070358 A3 | 7/2006 |

OTHER PUBLICATIONS

English-language translation of Chinese Search Report for corresponding Chinese application No. 2017800360329 dated Oct. 26, 2020 (2 pages).
Chinese First Office Action with English-language translation for corresponding Chinese application No. 2017800360329 dated Nov. 2, 2020 (16 pages).

* cited by examiner

CANNULATION DEVICE

The invention relates to a cannulation device for providing an access to a patient through a skin of the patient according to claim 1.

For placing a catheter in a human hollow organ, such as a visceral cavity (for example the gastro intestinal tract) through a patient's skin a cannulation device is used that is adapted to provide an access to the hollow organ through the patient's skin. The cannulation device comprises a puncture needle with a needle tip for puncturing the skin of the patient and a cannula for providing an access to the hollow organ through the puncture site.

From the state of the art a cannulation device with a puncture needle and a cannula is known wherein the tip of the puncture needle protrudes out of the cannula. The protruding needle tip may be a safety risk for the user as the user may hurt himself with the protruding tip by accident. Before puncturing the patient's skin the user may just cause a cutting injury with the needle tip. After puncturing the patient's skin and removing the cannulation device out of the patient's body, bacteria or viruses may be transmitted from the patient to the user additionally to the puncturing injury.

It is an object of the present invention to provide a cannulation device for providing an access to a patient through a skin of the patient that overcomes this safety risk.

To solve this problem the cannulation device of claim 1 is provided. This cannulation device comprises a puncture needle with a needle tip for puncturing the skin of the patient and a cannula. The puncture needle is movably connected to the cannula.

This allows a user to move the puncture needle with respect to the cannula such as to hide or cover the needle tip when desired, for instance before puncturing the patient's skin and after the patient's skin has been punctured and the cannulation device has been removed from the patient's body.

According to an aspect, the puncture needle is arranged at least partially inside the cannula and the puncture needle is movable inside the cannula along a longitudinal axis of the cannulation device. The puncture needle and the cannula may extend along the longitudinal axis of the cannulation device. The movable connection between the puncture needle and the cannula thus allows the puncture needle to slide within the cannula. For instance, the puncture needle may be movable between a puncture position, wherein the needle tip protrudes out of the cannula, and a safety position, wherein the needle tip is arranged inside the cannula. In the puncture position the puncture needle is adapted to puncture a patient's skin, while in the safety position the tip of the puncture needle is covered by the cannula avoiding that a user hurts himself with the needle tip. As long as the cannulation device is introduced in the patient the cannula provides an access to the hollow organ through the puncture site. Outside the patient the cannula serves as a protective cover of the needle tip. The cannula thus has a double function. The needle tip may be moved out of the safety position into the puncture position only during the puncture procedure.

According to an aspect, the puncture needle is secured to a needle holder and the cannula is secured to a cannula holder. The puncture needle and the cannula may both have a distal end that is provided to be introduced into the patient and a proximal end opposite the distal end. The puncture needle and the cannula may be secured to the needle holder and the cannula holder, respectively, at their proximal ends. For instance the needle holder and the cannula holder may have a common extension range along the longitudinal axis of the cannulation device. The needle holder and the cannula holder may at least partially extend concentrically about the longitudinal axis of the cannulation device. The needle holder may be movably, for instance slidably, mounted at the cannula holder. For this purpose the cannula holder (needle holder) may comprise a guiding channel for receiving a portion of the needle holder (cannula holder) that may be guided within this guiding channel along the longitudinal axis of the cannulation device with respect to the cannula holder (needle holder).

According to an aspect, the needle holder and the cannula holder each comprise at least one connecting element. The at least one connecting element of the needle holder and the at least one connecting element of the cannula holder are adapted to cooperate with each other such as to secure (lock) the needle holder with respect to the cannula holder in one or more defined position(s). The at least one connecting element of the needle holder and the at least one connecting element of the cannula holder may establish a detachable connection, for instance a latching connection. The at least one connecting element of the needle holder and the at least one connecting element of the cannula holder may be adapted to cooperate with each other such as to hold (lock) the puncture needle in the safety position. This ensures that the puncture needle and in particular the needle tip does not accidentally moves out of the cannula. Additionally the at least one connecting element of the needle holder and the at least one connecting element of the cannula holder may be adapted to cooperate with each other such as to hold (lock) the puncture needle in the puncture position. This may help the user to hold the puncture needle (in particular the needle tip) in a defined (locked) position with respect to the cannula during the puncture procedure facilitating the manipulation of the cannulation device during the puncture procedure. Alternatively, in the puncture position the puncture needle may not be locked with respect to the cannula.

For instance, one connecting element may be provided for the needle holder (cannula holder) and two connecting elements may be provided for the cannula holder (needle holder). The two connecting elements of the cannula holder (needle holder) may be arranged in a distance to each other on an axis that extends substantially along the longitudinal axis of the cannulation device. The connecting element of the cannula holder that is arranged further away from the needle tip may be in engagement with the connecting element of the needle holder, when the puncture needle is in the safety position, while the connecting element of the cannula holder that is arranged closer to the needle tip may be in engagement with the connecting element of the needle holder, when the puncture needle is in the puncture position. Accordingly, in case that the needle holder comprises two connecting elements and the cannula holder one connecting element, the connecting element of the needle holder that is arranged further away from (closer to) the needle tip may be in engagement with the connecting element of the cannula holder, when the puncture needle is in the puncture position (safety position). By way of example, the one of the needle holder and the cannula holder has been described with one connecting element and the other of the needle holder and the cannula holder has been described with two connecting elements in order to lock the puncture needle with respect to the cannula in two different positions (safety position and puncture position). However, the number of connecting elements of the other of the needle holder and the cannula holder may be different from (greater than) two, if a different (greater) number of locking positions needs to be provided. Also, the number of connecting elements of the one of the needle holder and the cannula holder may be different from one, for instance in order to enhance the force of cooperation between the connecting elements.

Alternatively, one connecting element may be provided for the needle holder and one connecting element may be provided for the cannula holder. The connecting elements may be in engagement with each other when the puncture needle is in the safety position.

The at least one connecting element of the needle holder (cannula holder) may be a protrusion and the at least one connecting element of the cannula holder (needle holder) may be a recess or opening adapted to receive the protrusion such as to lock the protrusion.

According to an aspect, the puncture needle is moved from the safety position towards/into the puncture position by applying a force on the needle holder. The force may be applied linearly, for instance axially along the longitudinal axis of the cannulation device (in a direction from the proximal end to the distal end of the puncture needle). This allows using the cannulation device with a single hand: while the cannulation device is hold in one hand (at its cannula holder and/or needle holder) the force may be applied linearly with a thumb of this hand. As an alternative, the force may be applied along a helical path for instance. The force applied on the needle holder may also serve to bring the at least one connecting element of the needle holder and the at least one connecting element of the cannula holder out of engagement. As the puncture needle is secured to the needle holder, the force applied to the needle holder directly correlates with the speed of the puncture needle and the distance over which the puncture needle is moved. This allows a user to control precisely the puncture needle avoiding injuries by applying a force on the needle holder in order to move the puncture needle from the safety position towards/into the puncture position.

According to a further aspect, a release device may be provided that is adapted to release the at least one connecting element of the needle holder (cannula holder) out of engagement with the at least one connecting element of the cannula holder (needle holder). This release device may be provided to disengage the connecting elements holding the puncture needle in the puncture position. After disengagement the puncture needle may be moved out of the puncture position into/towards the safety position. A further release device may be provided to disengage the connecting elements holding the puncture needle and the needle tip in the safety position. After disengagement the puncture needle may be moved out of the safety position into/towards the puncture position.

An elastic element may be provided that is adapted to move the puncture needle and the needle tip out of the puncture position into the safety position. For this purpose the elastic element may be deformable along the longitudinal axis of the cannulation device. For example, the elastic element may be a spring element, such as a compressible/extendable (plastic) element or a (metallic) coil spring that extends along the longitudinal axis of the cannulation device. The elastic element may be out of its equilibrium configuration (for example stretched or compressed) when the puncture needle is in the puncture position and in or closer to its equilibrium configuration when the puncture needle is in the safety position. The restoring force of the elastic element may be used to drive the puncture needle from the puncture position into/towards the safety position. The puncture needle and the needle tip thus reproducibly move from the puncture position into/towards the safety position without requiring any contribution by the user. The user may however control the release device for disengaging the connecting elements holding the puncture needle in the puncture position, thus allowing the elastic element to move (after disengagement) the puncture needle and the needle tip out of the puncture position into/towards the safety position. The elastic element may be arranged such with respect to the needle holder and the cannula holder that it is brought out of its equilibrium configuration by the movement of the needle holder with respect to the cannula holder when the puncture needle is moved into/towards the puncture position.

As an alternative the elastic element may be adapted to move the puncture needle out of the safety position into the puncture position. In this case, the elastic element is out of its equilibrium configuration (for example stretched or compressed) when the puncture needle is in the safety position and in or closer to its equilibrium configuration when the puncture needle is in the puncture position. The restoring force of the elastic element is thus used to drive the puncture needle from the safety position into/towards the puncture position. All aspects considered for the case where the elastic element is adapted to move the puncture needle out of the puncture position into the safety position apply vice versa to the present case where the elastic element is adapted to move the puncture needle out of the safety position into the puncture position.

According to a further aspect, the needle holder comprises a hollow channel that extends through the entire needle holder along the longitudinal axis of the cannulation device. The puncture needle may be arranged (with its proximal end) at least in a part of the hollow channel. The hollow channel may have at least partially an inner diameter that corresponds to the outer diameter of the puncture needle, such that the puncture needle is hold in the hollow channel by frictional force. Additionally, the puncture needle may be glued into the hollow channel The needle holder may further comprise a valve that is arranged in the hollow channel. The valve may be arranged in a distance to the proximal end of the puncture needle. The valve may be adapted to provide and block a fluid connection between the distal end of the puncture needle (that is intended to be inserted into the human body) on the one hand and the proximal end of the needle holder (that is intended to stay outside the human body) on the other hand.

According to a further aspect, the needle holder and the cannula holder form an assembly that is adapted to be gripped and hold by a user's hand allowing a user to manipulate the cannulation device with a single hand, for example.

Figure 2:
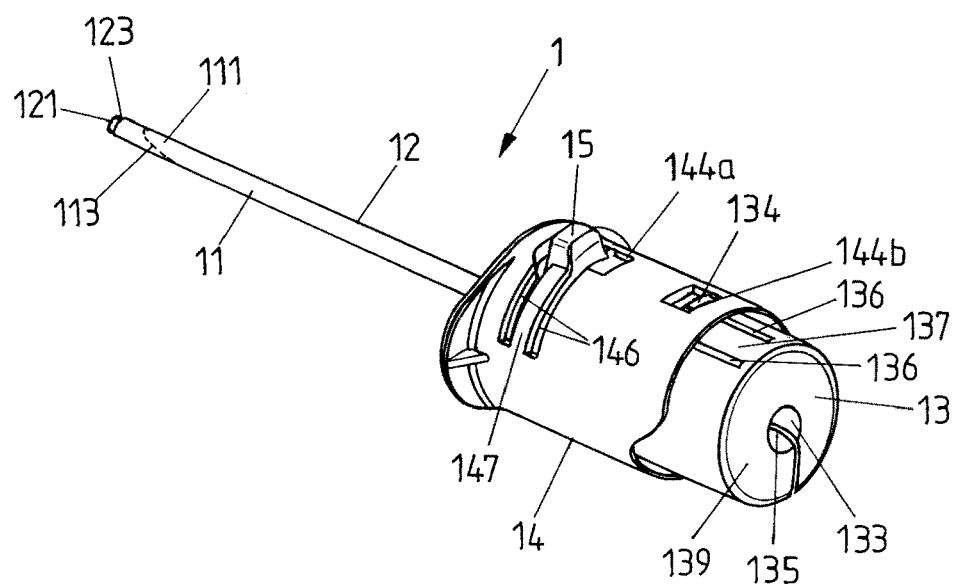
Figure 3:
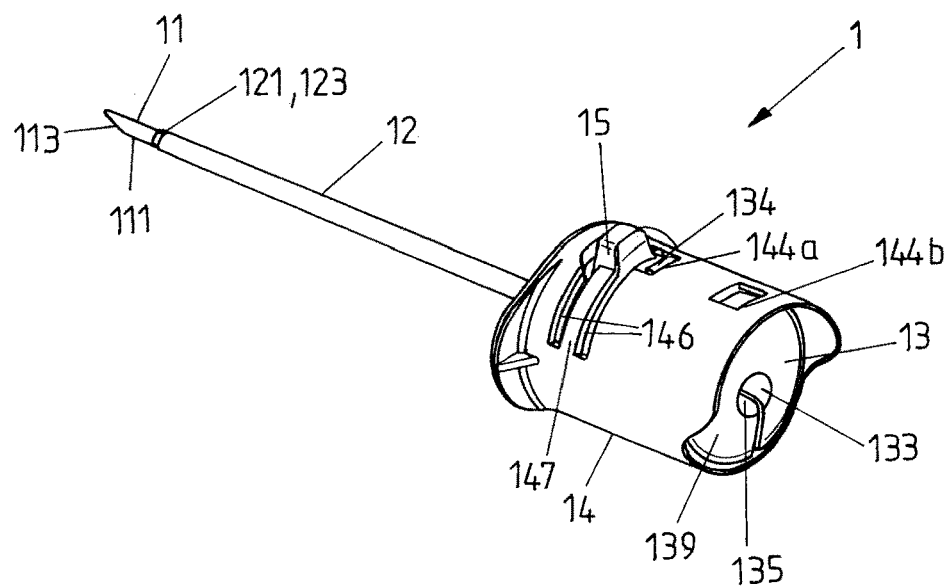

The idea underlying the invention is shown in the figures. The parts in the figures are not necessarily to scale, instead emphasis being placed upon illustrating principles of the invention. Moreover, in the figures, like reference numerals designate corresponding parts. In the drawings:

FIG. 1 schematically shows a cross-sectional view of a cannulation device according to an embodiment with a puncture needle and a cannula, wherein the puncture needle is in a safety position;

FIG. 2 schematically shows a perspective view of the cannulation device of FIG. 1, wherein the puncture needle is in the safety position; and FIG. 3 schematically shows a perspective view of the cannulation device of FIG. 1, wherein the puncture needle is in a puncture position.

In the following detailed description, reference is made to the accompanying drawings which form a part hereof and in which are shown by way of illustration specific embodiments in which the invention may be practiced.

In this regard, it is to be understood that other embodiments may be utilized and structural or logical changes may be made without departing from the scope of the present invention. The following detailed description, therefore, is not to be taken in a limiting sense, and the scope of the present invention is defined by the appended claims.

Reference will now be made in detail to various embodiments, one or more examples of which are illustrated in the figures. Each example is provided by way of explanation, and is not meant as a limitation of the invention. For example, features illustrated or described as part of one embodiment can be used on or in conjunction with other embodiments to yield yet a further embodiment. It is intended that the present invention includes such modifications and variations. The examples are described using specific language which should not be construed as limiting the scope of the appended claims. The drawings are not scaled and are for illustrative purposes only. For clarity, the same elements have been designated by the same references in the different drawings if not stated otherwise.

FIG. 1 shows a sectional view of a cannulation device 1 according to one embodiment. The cannulation device 1 comprises a puncture needle 11 for puncturing the skin of a patient and a cannula 12 for providing an access to a hollow organ of the patient through the puncture site once the skin of the patient has been punctured by the puncture needle 11. The puncture needle 11 and the cannula 12 are both hollow tubes that extend along a longitudinal axis L of the cannulation device 1. The puncture needle 11 is arranged at least partially inside the cannula 12.

The puncture needle 11 and the cannula 12 both have a distal end 111 (with a needle tip), 121 (with a tapered tip) and a proximal end 112, 122 opposite to the distal end 111, 121 (seen along the longitudinal axis L of the cannulation device 1). The distal ends 111, 121 are provided to be introduced into the patient. At the distal end 111 of the puncture needle 11 a needle tip 113 is provided. The needle tip 113 is sharp-edged, and in particular beveled, in order to puncture the patient's skin. At the distal end 121 of the cannula 12 a tapered tip 123 is provided. The tapered shape of the cannula 12 at its distal end allows for a smooth transition between the puncture needle 11 and the cannula 12.

The puncture needle 11 is slidably arranged inside the cannula 12. The puncture needle 11 is movable with respect to the cannula 12 between a safety position (FIGS. 1 and 2) in which the needle tip 113 is arranged inside the cannula 12 and a puncture position (FIG. 3) in which the needle tip 113 protrudes out of the cannula 12.

The puncture needle 11 is secured (at its proximal end 112) to a needle holder 13 while the cannula 12 is secured (at its proximal end 122) to a cannula holder 14. The puncture needle 11 and the cannula 12 are immovably attached to the needle holder 13 and the cannula holder 14, respectively. The needle holder 13 and the cannula holder 14 are dimensioned such that the cannulation device 1 can be hold and manipulated by a user at the needle holder 13/cannula holder 14. As the needle holder 13 is immobile with respect to the puncture needle 11 and the cannula holder 14 is immobile with respect to the cannula 12, while the puncture needle 11 is slidable with respect to the cannula 12, also the needle holder 13 is slidable with respect to the cannula holder 14. The puncture needle 11 can thus be moved between the puncture position and the safety position by manipulating the needle holder 13 and/or cannula holder 14.

The cannula holder 14 is formed by a hollow body of substantially cylindrical shape that comprises a guiding channel 141 for receiving a portion of the needle holder 13 that is guided within the guiding channel 141 along the longitudinal axis L of the cannulation device 1 with respect to the cannula holder 14. The guiding channel 141 has a substantially annular cross section (in a plane perpendicular to the longitudinal axis L of the cannulation device 1) and is limited by two substantially cylindrical side walls (an inner side wall and an outer side wall). At its distal and proximal ends (oriented towards and away from the distal end 121 of the cannula 12) the cannula holder 142 comprises a stop element 142 that protrudes substantially perpendicularly to the longitudinal axis L of the cannulation device 1 into the guiding channel 141 such as to limit the path of the needle holder 13 inside the cannula holder 14. The distance along the longitudinal axis L may define the length of the path. At its proximal end the cannula holder 14 is open such that the guiding channel 141 may receive a portion of the needle holder 13. At its distal end the cannula holder 14 further comprises a sleeve 143 for holding the proximal end 122 of the cannula 12. The sleeve 143 extends substantially centrally inside the cylindrical side walls of the cannula holder 14 along the longitudinal axis L. The sleeve 143 has an inner diameter that corresponds to the outer diameter of the cannula 12, such that the cannula 12 may be hold by the sleeve 143 by frictional forces.

The needle holder 13 is also formed by a hollow body of substantially cylindrical shape. The substantially cylindrical side wall of the needle holder is dimensioned such that it is adapted to slide within the guiding channel 141 of the cannula holder 14 along the longitudinal axis L of the cannulation device 1. At its proximal end the needle holder 13 comprises a sleeve 133 for holding the proximal end 112 of the puncture needle 11. The sleeve 133 extends substantially centrally inside the cylindrical side wall of the needle holder 13 along the longitudinal axis L. The sleeve 133 is connected to the cylindrical side wall of the needle holder 13 by a push-surface 139 that extends substantially perpendicular to the longitudinal axis L. The push-surface 139 may be used to manually push the needle holder 13 into the cannula holder 14. The push-surface 139 has the shape of a disk that extends over the entire gap between the cylindrical side wall of the needle holder 13 and the sleeve 133. Alternatively, the disk may also extend only over a portion of that gap.

The sleeves 133 and 143 are arranged coaxially with respect to each other such that the puncture needle 11 extends inside the cannula 12. The sleeves 133, 143 hold the puncture needle 11 and the cannula 12, respectively, by frictional forces.

In order to lock the puncture needle 11 in the safety position and in the puncture position, the needle holder 13 and the cannula holder 14 comprise connecting elements 134, 144a and 144b. By way of example the needle holder 13 comprises one connecting element 134 arranged on its side wall and the cannula holder 14 comprises two connecting elements 144a, 144b arranged on its outer side wall. The connecting elements 144a, 144b of the cannula holder 14 are arranged in a distance to each other along an axis that extends substantially parallel to the longitudinal axis L. On the one hand, the connecting element 134 of the needle holder 13 is adapted to cooperate with the connecting element 144a of the cannula holder 14 (that is closer to the distal end 121 of the cannula 12 than the connecting element 144*b*) in order to hold the puncture needle 11 in the puncture position. On the other hand, the connecting element 134 of the needle holder 13 is adapted to cooperate with the connecting element 144*b* of the cannula holder 14 (that is further away from the distal end 121 of the cannula 12 than the connecting element 144*a*) in order to hold the puncture needle 11 in the safety position. In the embodiment shown in FIG. 1, the connecting element 134 of the needle holder 13 is a protrusion that protrudes from the side wall of the needle holder 13 and extends in an angle to the longitudinal axis L towards the outer side wall of the cannula holder 14. The two connecting elements 144*a*, 144*b* of the cannula holder 14 are openings in the outer side wall of the cannula holder 14 that are adapted to receive the protrusion 134.

The shape (in particular the ratio of material thickness to the length along the longitudinal axis L) of the side wall of the needle holder 13 is chosen such to provide the side wall sufficient elasticity to bend when the protrusion 134 is entering or leaving one of the openings 144*a*, 144*b* or when the protrusion 134 is moving/located between the openings 144*a*, 144*b*. In order to enhance the elasticity, the side wall may comprise two grooves 136 that extend along the longitudinal axis L on both sides of the protrusion 134 (FIG. 2). The grooves 136 define an oblong section 137 that extends along the longitudinal axis L and that supports the protrusion 134. The oblong shape of the section 137 allows this section to elastically bend with respect to the residual side wall of the needle holder 13 when the protrusion 134 is entering or leaving one of the openings 144*a*, 144*b* or when the protrusion 134 is moving/located between the openings 144*a*, 144*b*. The grooves 136 extend through the entire thickness of the side wall. As an alternative, the grooves 136 may be formed by reducing the material thickness of the side wall. As a further alternative the side wall of the needle holder 13 may be less elastic, but the protrusion 134 itself may be made of a material that has an elasticity allowing the protrusion 134 to deform (compress) when the protrusion 134 is leaving one of the openings 144*a*, 144*b* or when the protrusion 134 is moving/located between the openings 144*a*, 144*b* and to deform (expand) when the protrusion 134 is entering one of the openings 144*a*, 144*b*.

The protrusion 134 is moved out of engagement with the opening 144*b* (safety position) by pushing the needle holder 13 (at the push-surface 139) along the longitudinal axis L in a direction from the proximal end 112 to the distal end 111 of the puncture needle 11. The shape of the protrusion 134 allows the protrusion to slide out of the opening 144*b* when the needle holder 13 is pushed as described. When pushing the needle holder 13 further, the protrusion 134 moves from the opening 144*b* to the opening 144*a*. The elasticity of the side wall of the needle holder 13 (of the oblong section 137) allows the side wall (the oblong section 137) to slightly bend inside as long as the protrusion 134 is moving from the opening 144*b* to the opening 144*a*. When pushing the needle holder 13 further, the elasticity of the side wall of the needle holder 13 (of the oblong section 137) pushes the protrusion outwardly into engagement with the opening 144*a* (puncture position).

In order to release the protrusion 134 out of engagement with the opening 144*a* (puncture position) a release device 15 is provided at the outer side wall of the cannula holder 14 such that it is accessible for a user. The release device 15 is spring-mounted to the cannula holder 14. In the embodiment shown in FIGS. 2 and 3 the release device 15 is a protrusion formed on the outside of the outer side wall of the cannula holder 14. The outer side wall of the cannula holder 14 comprises two grooves 146 that extend in an angle to the longitudinal axis L on both sides of the release device 15. The grooves 146 define an oblong section 147 that extends in an angle to the longitudinal axis L and that supports the release device 15. The oblong shape of the section 147 allows this section to elastically bend with respect to the residual outer side wall of the cannula holder 14 upon application of a force on the release device 15. The grooves 146 extend through the entire thickness of the outer side wall. As an alternative, the grooves 146 may be formed by reducing the material thickness of the outer side wall.

The elasticity of the connection between the release device 15 and the cannula holder 14 (o the oblong section 147) allows the release device 15 to move (upon application of a corresponding force by a user) substantially perpendicularly to the longitudinal axis L from its rest position towards the protrusion 134 in order to push the protrusion 134 out of the opening 144*a*. When the user ceases to apply the force to the release device 15 the release device returns into its rest position.

In order to move the puncture needle 11 from the puncture position into the safety position once the engagement of the protrusion 134 and the opening 144*a* has been released, an elastic element 16 is provided. In the embodiment of FIG. 1 the elastic element 16 is a coil spring that extends along the longitudinal axis L. The elastic element 16 is arranged between the inner side wall of the cannula holder 14 and the sleeve 143 of the cannula holder 14. The elastic element 16 also extends around the sleeve 133 of the needle holder 13. When the puncture needle 11 is in the puncture position, the coil spring 16 is out of its equilibrium configuration (compressed). Once the engagement of the protrusion 134 and the opening 144*a* has been released, the compressed coil spring 16 urges the needle holder 13 (in a direction from the distal end 111 to the proximal end 112 of the puncture needle 11) towards the safety position. When the puncture needle 11 has reached its safety position, the coil spring 16 is in or closer to its equilibrium configuration. Once the puncture needle 11 has reached the safety position the protrusion 134 engages the opening 144*b* due to the elasticity of the side wall of the needle holder 13 (of the oblong section 137 of the needle holder 13).

The needle holder 13 comprises a hollow channel 135 that extends through the entire needle holder 13 along the longitudinal axis L and substantially centrally through the sleeve 133. The puncture needle 11 that is hold by the sleeve 133 is arranged in a part of the hollow channel 135. When the cannulation device 1 is introduced in a hollow organ of a patient through the patient's skin, the hollow channel 135 in combination with the puncture needle 11 forms a fluid communication between the hollow organ and the patient's environment. As the hollow organ needs to be insufflated for placing a catheter, gas that is present in the hollow organ may flow out of the hollow organ through this fluid communication when puncturing the patient. In order to avoid that the insufflation gas flows out of the hollow organ, a valve 138 is arranged in the hollow channel 135 in a part of the sleeve 133. The valve 138 may be designed such that it allows insufflation of the hollow organ through the hollow channel 135 and the puncture needle 11.

FIG. 2 shows a perspective view of the cannulation device 1 of FIG. 1 with the puncture needle 11 in the safety position and FIG. 3 shows a perspective view of the cannulation device 1 of FIG. 1 with the puncture needle 11 in the puncture position. Generally, the outer diameter of the puncture needle 11 and the inner diameter of the cannula 12 are substantially identical and constant over the entire length (along the longitudinal axis L) in order to avoid the formation of a channel between the puncture needle 11 and the cannula 12. As an alternative the outer diameter of the puncture needle 11 is constant over the entire length and the inner diameter of the cannula 12 changes over its length, wherein the inner diameter of the cannula 12 is in at least one section (for instance at the distal end 121 of the cannula 12) of the cannula 12 substantially identical to the outer diameter of the puncture needle 11.

The invention claimed is:

1. A cannulation device for providing an access to a patient through a skin of the patient, comprising a puncture needle with a needle tip for puncturing the skin of the patient and a cannula, the puncture needle being secured to a needle holder and the cannula being secured to a cannula holder so that the needle and the cannula extend along a longitudinal axis of the cannulation device, with the needle holder being movably mounted with respect to the cannula holder so that puncture needle is movable between a puncture position, in which the needle tip protrudes out of the cannula, and a safety position, in which the needle tip is arranged inside the cannula, the needle holder comprising a first connecting element and the cannula holder comprising spaced-apart second and third connecting elements arranged at a distance to each other along an axis that extends substantially parallel to the longitudinal axis, the first connecting element comprising a protrusion and each of the second and third connecting elements comprising a window sized to receive the protrusion, wherein the first connecting element of the needle holder and the second connecting element of the cannula holder are adapted to cooperate with each other such as to secure the needle holder with respect to the cannula holder, with the puncture needle in the safety position, and the first connecting element of the needle holder and the third connecting element of the cannula holder are adapted to cooperate with each other to secure the needle holder with respect to the cannula holder with the puncture needle in the puncture position.

2. The cannulation device according to claim 1, wherein the puncture needle is arranged at least partially inside the cannula and wherein the puncture needle is movable inside the cannula along a longitudinal axis of the cannulation device.

3. The cannulation device according to claim 1, wherein the first connecting element of the needle holder is brought out of engagement with the second connecting element of the cannula holder for moving the puncture needle out of the safety position into the puncture position by applying a force on the protrusion associated with the needle holder.

4. The cannulation device according to claim 1, further comprising an elastically moveable release device that is adapted to engage the protrusion of the first connecting element of the needle holder to release the first connecting element out of engagement with the second connecting element of the cannula holder for moving the puncture needle out of the puncture position into the safety position.

5. The cannulation device of claim 4, wherein the cannula holder comprises a side wall having a pair of spaced-apart grooves extending at an angle to a longitudinal axis defined by the cannulation device and the elastically movable release device comprises a protrusion positioned on the surface of the cannula holder side wall between the spaced-apart grooves.

6. The cannulation device according to claim 1, further comprising an elastic element adapted to move the puncture needle from the puncture position into the safety position.

7. The cannulation device according to claim 6, wherein the elastic element is out of an equilibrium configuration when the puncture needle is in the puncture position and in or closer to the equilibrium configuration when the puncture needle is in the safety position.

8. The cannulation device according to claim 1, wherein the needle holder comprises a hollow channel that extends through the entire needle holder and in that the puncture needle is arranged in a part of the hollow channel.

9. The cannulation device according to claim 8, wherein the needle holder comprises a valve that is arranged in the hollow channel that permits flow of insufflation through the hollow needle in a first direction and prevents the flow of insufflation gas through the needle in a second direction opposite to the first direction.

10. The cannulation device according to claim 1, wherein the needle holder and the cannula holder form an assembly that is configured to be gripped and held by a user's hand.

11. The cannulation device of claim 1, wherein the needle holder comprises a side wall with the protrusion defining the first connecting element formed thereon, the side wall being elastically bendable to permit the protrusion to move between the windows on the cannula holder defining the second and third connecting elements.

12. The cannulation device of claim 11, wherein the side wall of the needle holder further comprises two longitudinally extending grooves that define an oblong section that supports the protrusion defining the first connecting element.

* * * * *